United States Patent
Huang et al.

(10) Patent No.: US 9,310,474 B2
(45) Date of Patent: Apr. 12, 2016

(54) PORTABLE ULTRASOUND IMAGING DEVICES

(71) Applicant: CHISON MEDICAL IMAGING CO., LTD., Wuxi, Jiangsu Province (CN)

(72) Inventors: Mingjin Huang, Wuxi (CN); Feng Zhou, Wuxi (CN)

(73) Assignee: Chison Medical Imaging, Inc., Jiangsu (CN)

( * ) Notice: Subject to any disclaimer, the term of this patent is extended or adjusted under 35 U.S.C. 154(b) by 528 days.

(21) Appl. No.: 13/909,087

(22) Filed: Jun. 4, 2013

(65) Prior Publication Data
US 2014/0355374 A1 Dec. 4, 2014

(51) Int. Cl.
*A61B 8/02* (2006.01)
*G01S 7/52* (2006.01)
*A61B 8/00* (2006.01)

(52) U.S. Cl.
CPC ............ *G01S 7/52079* (2013.01); *A61B 8/4427* (2013.01); *A61B 8/462* (2013.01); *Y10T 16/5323* (2015.01)

(58) Field of Classification Search
CPC .... A61B 19/5244; A61B 18/14; A61B 18/02; A61B 19/5212; A61B 8/12; A61B 18/1492; A61B 19/54; A61B 8/4427; A61B 8/462; G01S 7/52; G01S 7/52079; Y10T 16/5323
USPC .......... 367/11; 16/239; 248/351; 128/200.16, 128/900–916
See application file for complete search history.

(56) References Cited

U.S. PATENT DOCUMENTS

| 5,942,978 A * | 8/1999 | Shafer ................ E05B 73/0017 340/10.5 |
| 5,943,890 A * | 8/1999 | Field ................... E05B 27/0039 70/337 |
| 2005/0154303 A1 * | 7/2005 | Walker ................ G01S 15/8979 600/443 |

OTHER PUBLICATIONS

Philips VISIQ system Video http://www.healthcare.philips.com/main/products/ultrasound/systems/visiq/#&&/wEXAQUOY3V-ycmVudFRhYIBhdGgFEERIdGFpbHM6T3ZIcnZpZXXdwGB6s-7Z5i1iyK2qCyu+ZIAjHM5w== date: 2015.*

(Continued)

*Primary Examiner* — Luke Ratcliffe
*Assistant Examiner* — Amienatta M Ndure Jobe
(74) *Attorney, Agent, or Firm* — Finnegan, Henderson, Farabow, Garrett & Dunner, LLP

(57) ABSTRACT

A portal ultrasound imaging apparatus having an adjustable hinge assembly, which includes a key having a narrower end and an end wider in the circumferential direction of the hinge assembly. The key is movable in a slot in an axial direction of the hinge assembly to a locked position, where the side surfaces of the key presses against the walls of the slot to eliminate circumferential gaps between the key and the slot. When at the locked position in the slot, the key can be pushed towards the opposite of the axial direction to an unlocked position where an angular lock of the hinge assembly is released, allowing the hinge assembly to be adjusted to a desired angular coupling. The key can then be pushed in the axial direction back to the locked position in the slot to prevent change in the coupling angle of the hinge assembly.

20 Claims, 10 Drawing Sheets

(56) References Cited

OTHER PUBLICATIONS

KX5200 Veterinary Ultrasound Scanner Portable Ultrasound Livestock Pet Cattle Animals Ultrasound With Battery 6.5MHz Rectal Probe http://www.dhgate.com/store/product/kx5200-veterinary-ultrasound-scanner-portable/246912128.html Copyright Notice © 2004-2015 DHgate.com All rights reserved.*
David Lenovo Yoga Tablet 2 Teardown Nov. 8, 2014 http://www.myfixguide.com/manual/lenovo-yoga-tablet-2-disassembly/.*

* cited by examiner

PORTABLE ULTRASOUND IMAGING DEVICES

FIELD OF THE TECHNOLOGY

The present disclosure relates to ultrasound imaging devices in general, and more particularly but not limited to, portal devices with adjustable support components.

BACKGROUND

Chinese Patent Application Nos. 201110178175.8 and 201120223929.2, published Jan. 4, 2012 and Mar. 7, 2013 respectively, and entitled "Handheld ultrasonic diagnostic apparatus", discloses portable ultrasonic diagnostic devices that have an adjustable support component.

SUMMARY OF THE DESCRIPTION

Some embodiments are summarized in this section.

In one aspect, a portable ultrasound imaging apparatus includes: a housing; a display device amounted on the housing; a processor disposed within the housing and coupled with the display device to present ultrasound images; a beamformer disposed within the housing and coupled with the processor to control an ultrasound transducer; a support component hingedly coupled with the housing to allow the support component to rotate with respect to the housing about an axis parallel to an edge of the display device; and an adjustable assembly coupled between the support component and the housing.

When the adjustable assembly is in a first configuration, the support component is locked to the housing with respect to rotation about the axis. When the adjustable assembly is in a second configuration, the support component is rotatable about the axis with respect to the housing.

The adjustable assembly can include: a key extending in parallel to the axis; and walls extending in parallel to the key to define a slot configured to accommodate the key. When the key moves in a first direction parallel to the axis to a first position in the slot, at least a portion of side surfaces of the key is in contact with the walls to prevent the key from moving in the slot in the first direction beyond the first position; when the key is at the first position in the slot, the adjustable assembly is locked in the first configuration, and the key is movable in a second direction opposite to the first direction to a second position in the slot to provide a gap between the walls and the side surfaces of the key; and when the key is at the second position in the slot, the adjustable assembly is in the second configuration and allows the support component to rotatable about the axis with respect to the housing.

For example, the key has a first end and a second end; the key extending from the first end to the second end in the first direction; a width of the second end of the key is smaller than a width of the first end of the key; the side surfaces of the key extends from the first end to the second end; and the side surfaces are separated in a circumferential direction about the axis.

For example, a height of the second end of the key in a radial direction about the axis is equal to a height of the first end of the key in the radial direction about the axis. In another example, a height of the second end of the key in a radial direction about the axis is smaller than a height of the first end of the key in the radial direction about the axis.

For example, when the key is at the first position in the slot, a distance between the walls at the first end of the key is equal to the width of the first end of the key, and a distance between the walls at the second end of the key is equal to the width of the second end of the key.

For example, the adjustable assembly includes a spring element configured to push the key in the first direction.

For example, the adjustable assembly further includes a push knob configured to be pushed by a user against the spring element to move the key in the second direction.

For example, when the key is at the first position in the slot, the gap is eliminated.

For example, the an adjustable assembly further includes a first set of teeth and a second set of teeth corresponding to the first set of teeth; both the first set of teeth and the second set of teeth are evenly distributed in a circumferential direction about the axis; when the key is at the first position in the slot, the first set of teeth engages with the second set of teeth to lock the support component to the housing with respect to rotation about the axis; and when the key is at the second position in the slot, the first set of teeth disengages with the second set of teeth to allow the support component rotate about the axis with respect to the housing.

For example, the housing includes a back cover; the walls defining the slot are fixedly coupled with the support component; the first set of teeth is fixedly coupled with the back cover; and the second set of teeth is fixedly coupled with the key.

For Example, adjustable assembly further includes a tubular component having a first end and a second end; the first end of the tubular component is hingedly coupled with the back cover and rotatable about the back cover along the axis; and the key is on an outer surface of the second end of the tubular component.

For example, the second set of teeth is formed on the tubular component.

In another aspect, a portable display apparatus includes: a display device; a support component hingedly coupled with the display device to allow the support component to rotate with respect to the display device along an axis; and an adjustable assembly coupled between the support component and the display device.

The adjustable assembly may include: a key having a first end and a second end, the key extending from the first end to the second end in a first direction parallel to the axis, the key having side surfaces extending from the first end to the second end, the side surfaces of the key separated by a distance in a circumferential direction about the axis; and walls substantially in parallel with the side surfaces of the key to define a slot for the key.

When the key moves along the first direction to a first position in the slot, contacting between at least a portion of the side surfaces of the key and the walls prevents the key from moving in the first direction in the slot beyond the first position; when the key is at the first position in the slot, the key is movable only in a second direction opposite to the first direction, the key movable in the second direction to a second position in the slot; when the key is at the first position in the slot, the support component is locked to the display device with respect to rotation along the axis; and when the key is at the second position in the slot, the support component is rotatable along the axis with respect to the display device.

For example, a width of the second end of the key is smaller than a width of the first end of the key.

For example, when the key is at the first position in the slot, a distance between the walls at the first end of the key is equal to the width of the first end of the key, and a distance between the walls at the second end of the key is equal to the width of the second end of the key.

For example, the adjustable assembly can include: a spring element configured to push the key in the first direction; a push knob configured to be pushed by a user against the spring element to move the key in the second direction; a first set of teeth evenly distributed along a circumferential direction about the axis; and a second set of teeth evenly distributed along a circumferential direction about the axis. When the key is at the first position in the slot, the first set of teeth are in gaps between second set of teeth, and the second set of teeth are in gaps between first set of teeth to look the support component to the display device with respect to rotation about the axis; and when the key is at the second position in the slot, the first set of teeth and the second set of teeth are not in contact with each other to allow the support component to rotate about the axis with respect to the display device.

For example, the display device includes a back cover; the first set of teeth is fixedly coupled with the back cover; the walls defining the slot are fixedly coupled with the support component; and the second set of teeth is fixedly coupled with the key.

For example, adjustable assembly further includes a tubular component having a first end and a second end; the first end of the tubular component is hingedly coupled with the back cover and rotatable about the back cover along the axis; and the key is positioned on an outer surface of the second end of the tubular component.

For example, the set of teeth is formed on the tubular component; and the component defining a set of slots is disposed along the axis between the set of teeth and the key.

In a further aspect, an adjustable hinge assembly includes: a tubular component having a first end and a second end, the tubular component extending from the first end to the second end in a first direction along an axis and having 1) a key formed on the second end and extending in parallel to the axis, the key having side surfaces extending in the first direction and separated by a distance in a circumferential direction about the axis, and 2) a plurality of first teeth evenly distributed in the circumferential direction about the axis. The adjustable hinge assembly includes: a first component having a ring structure defining an opening configured to accept the second end of the tubular component, the ring structure having walls extending in the first direction and separated by a distance in the circumferential direction about the axis, the walls defining a slot for the key; a second component having a plurality of second teeth corresponding to the plurality of the first teeth and evenly distributed in the circumferential direction about the axis; a spring element configured to push the tubular component in the first direction; and a push knob coupled with the second end of the tubular component to allow a user to push against the spring element to move the tubular component in a second direction opposite to the first direction.

When the spring element pushes the tubular component in the first direction to a first position, contacting between the side surfaces of the key and the walls prevents the tubular component from moving further in the first direction beyond the first position; and the plurality of first teeth engages with the plurality of second teeth to lock the first component with respect to the second component with respect to rotation about the axis;

When the push knob is pushed to move tubular component in the second direction to a second position, a gap is provided between the side surfaces of the key and the walls defining the slot; and the plurality of first teeth disengages with the plurality of second teeth to allow the first component to rotate about the axis relative to the second component.

For example, the key has a first key end and a second key end; the key extending from the first key end to the second key end in the first direction; the side surfaces are separated by: a first distance in the circumferential direction about the axis at the first key end; and a second distance in the circumferential direction about the axis at the second key end, where the first distance is larger than the second distance.

Other features will be apparent from the accompanying drawings and from the detailed description which follows.

BRIEF DESCRIPTION OF THE DRAWINGS

The embodiments are illustrated by way of example and not limitation in the figures of the accompanying drawings in which like references indicate similar elements.

DETAILED DESCRIPTION

The following description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment; and, such references mean at least one.

Figure 1:
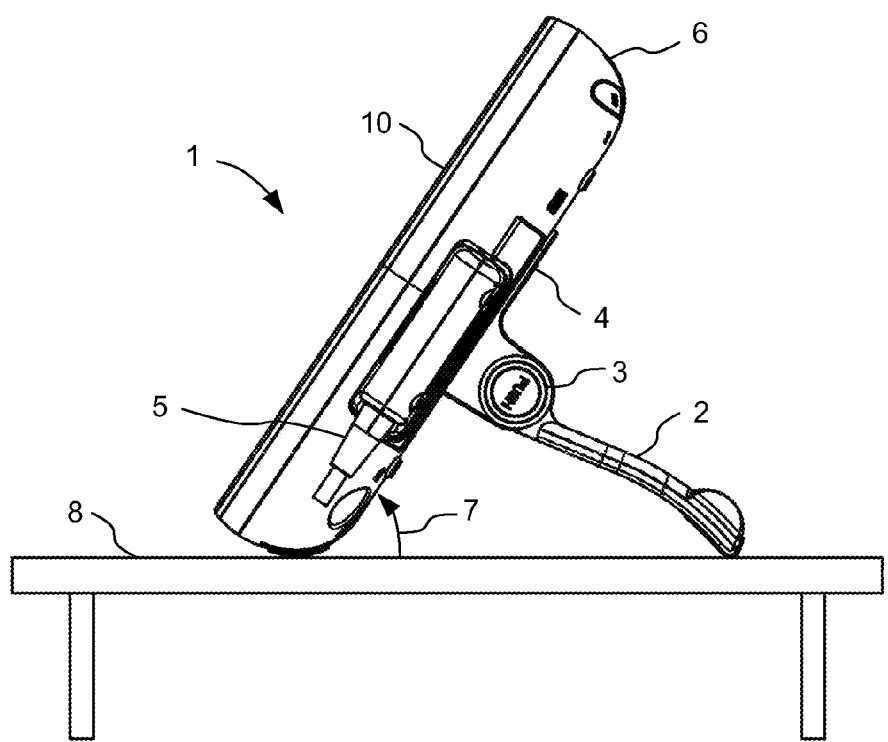
FIGS. 1 and 2 illustrate a portable ultrasound imaging apparatus having an adjustable support component adjustable and locked to different positions relative to the housing of the portable ultrasound imaging apparatus
Figure 2:
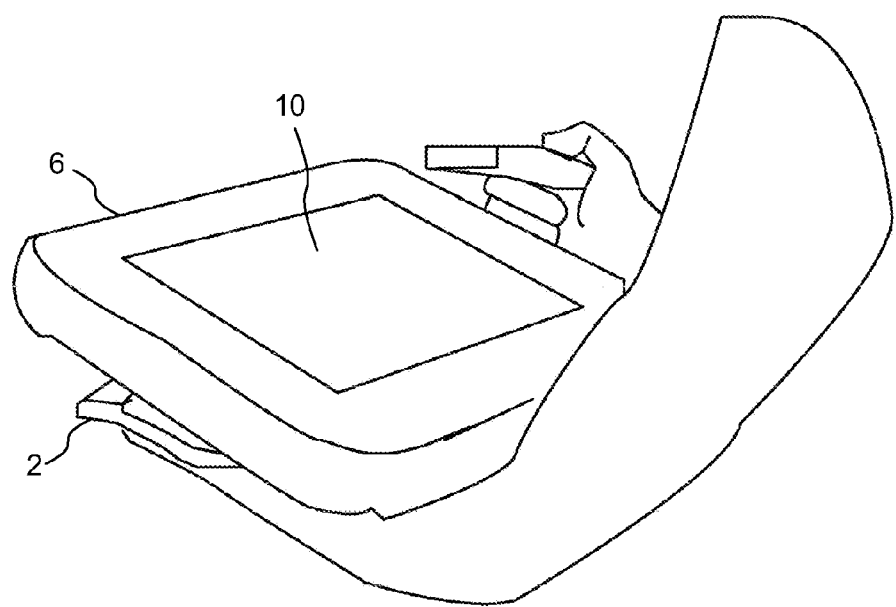

FIGS. 1 and 2 illustrate a portable ultrasound imaging apparatus having an adjustable support component adjustable and locked to different positions relative to the housing of the portable ultrasound imaging apparatus.

In FIG. 1, a portable ultrasound imaging apparatus 1 includes a housing 6 and a support component 2. The support component 2 is hingedly 3 coupled to a back cover 4 of the housing 6.

The portable ultrasound imaging apparatus 1 has a display device 10 mounted on the front side of the housing 6, a processor disposed within the housing 6 and coupled with the display device 10 to present ultrasound images, and a beamformer disposed within the housing 6 and coupled with the processor to control an ultrasound transducer 5.

In FIG. 1, the hinge coupling 3 between the back cover 4 and the support component 2 is adjusted to, and locked at, an angle suitable for placing the portal ultrasound imaging apparatus 1 on a flat surface 8 in a position where the display device 10 is raised up to an angle 7 on the surface 8 for viewing. The angle 7 is adjustable via adjusting the coupling angle between the back cover 4 and the support component 2.

In FIG. 1, the ultrasound transducer 5 is attached to the side of the housing 6. The ultrasound transducer 5 can be detached from the housing 6 for handheld operations, as illustrated in FIG. 2.

In FIG. 2, the support component 2 is adjusted to a position to allow the portable ultrasound imaging apparatus 1 to rest on an arm of a user.

Figure 3:
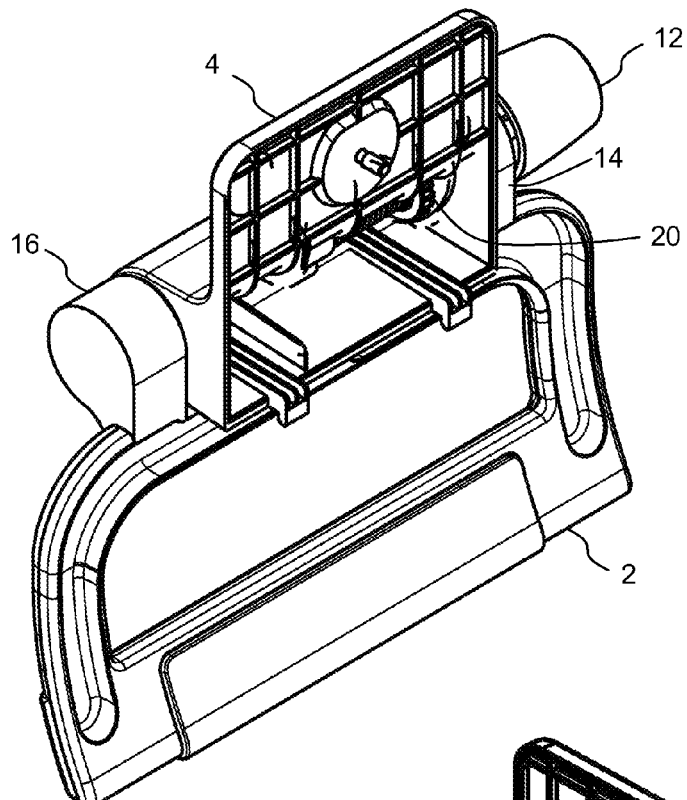
FIGS. 3-4 illustrate an adjustable support component coupled with a back cover of a portable ultrasound image apparatus.
Figure 4:
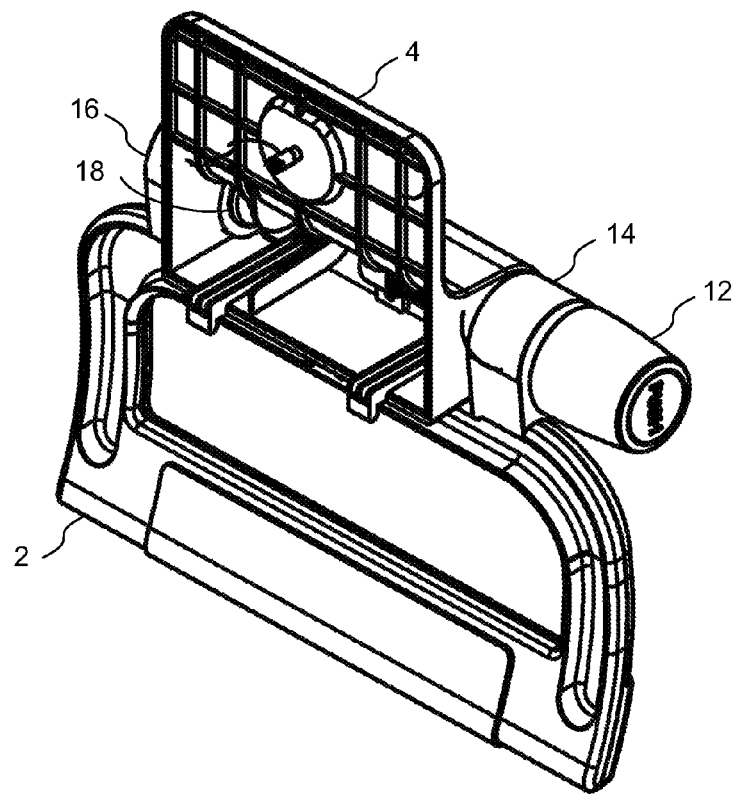

FIGS. 3-4 illustrate an adjustable support component coupled with a back cover of a portable ultrasound image apparatus.

In FIG. 3, the back cover 4 is hingedly coupled with the support component 2 via a ring structure 14, and an angular locking mechanism 20, and a hinge support 16. The ring structure 14 and the hinge support 16 are fixedly coupled with the support component 2.

In FIG. 3, a push knob 12 is coupled with locking mechanism 20. The push knob can be pushed towards the hinge support 16 to release the angular locking mechanism 20. When the angular locking mechanism 20 is released, the back cover 4 can be rotated relative to the support component 2 along an axis along the center of the hinge support 16 to the center of the ring structure 14.

FIG. 4 shows a tubular element 18 hingedly coupled the left side of the back cover 14 to the hinge support 16. The coupling among the hinge support 16, the left side of the back cover 14 and the tubular element 18 allows the left side of the back cover 14 to rotate freely about the axis relative to the hinge support 16.

Figure 9:
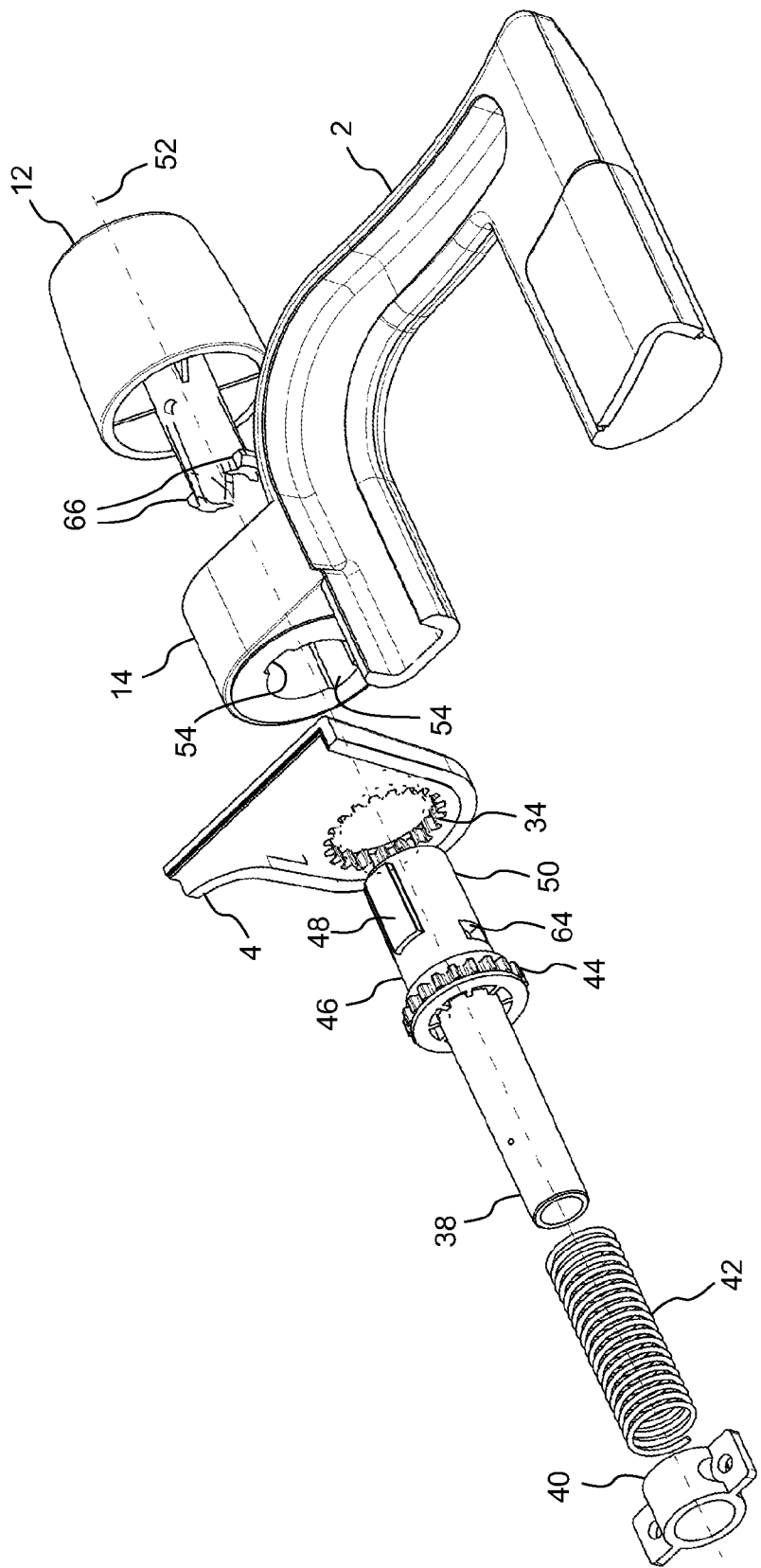
FIG. 9 shows an exploded view of an adjustable hinge assembly according to one embodiment.

Details of the locking mechanism 20 are illustrated in FIG. 9 and other figures and discussed further below.

Figure 5:
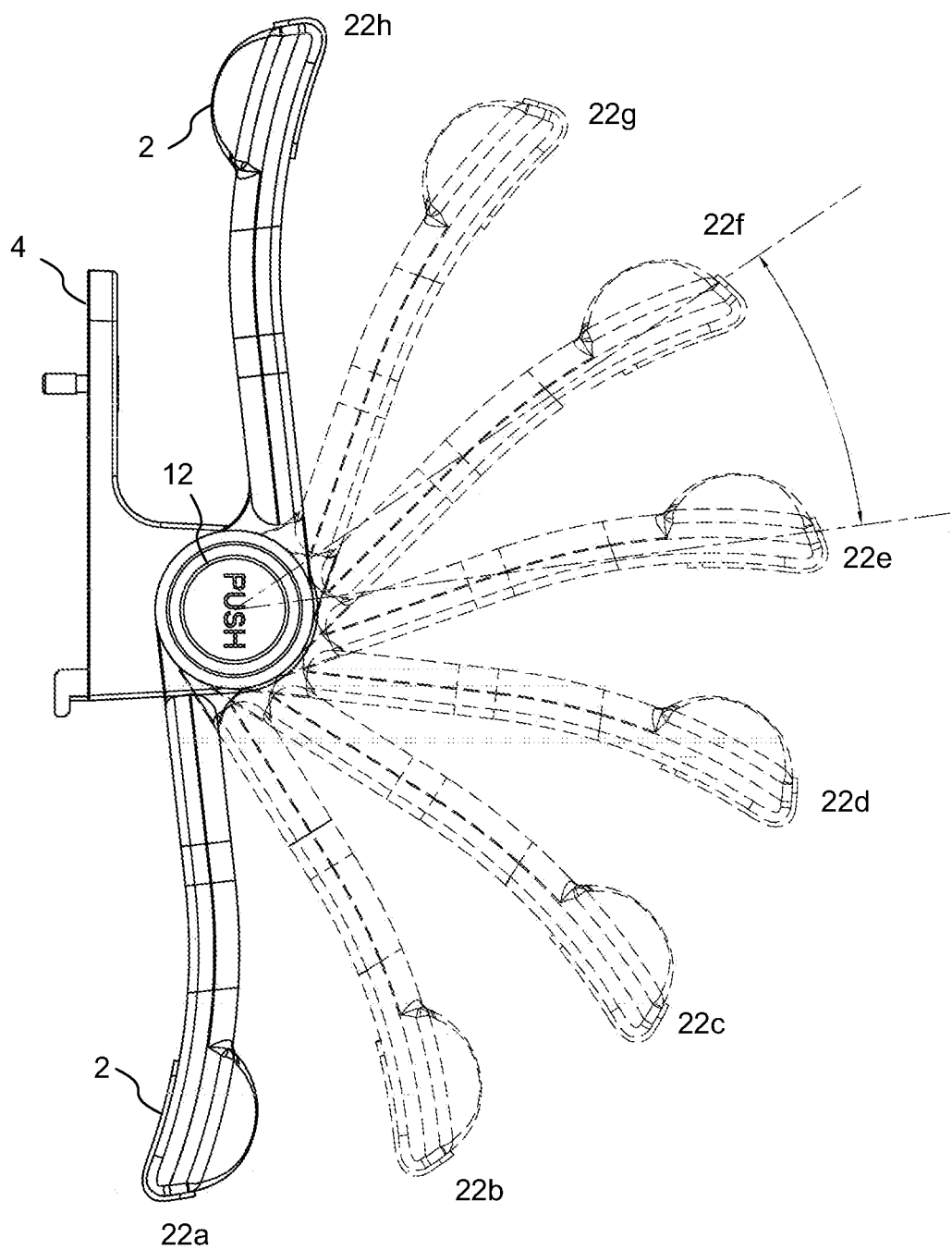
FIG. 5 illustrates adjustable positions of an adjustable support component with respect to a back cover.

FIG. 5 illustrates adjustable positions of the adjustable support component 2 with respect to the back cover 4. In FIG. 5, the push knob 12 can be pushed in to release the locking mechanism 20 and thus allow the support component 2 to be rotated to various positions (e.g., 22a to 22h) relative to the back cover 4. After the support component 2 is adjusted to a desirable position (e.g., from 22e to 22f), the pressure on the push knob 12 can be released to engage the locking mechanism 20.

When the locking mechanism 20 is engaged, the locking mechanism 20 prevents the support component 2 from rotating relative to the back cover 4.

Figure 6:
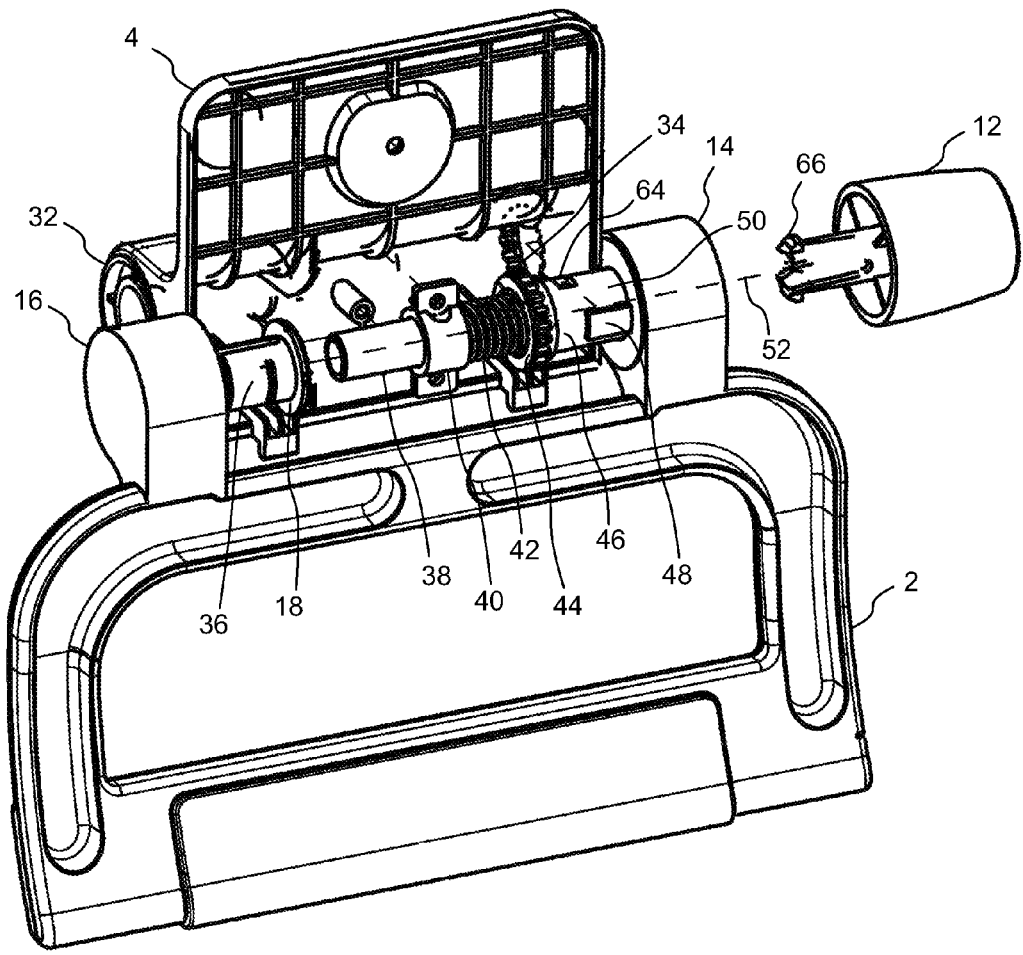
FIG. 6 shows components of an adjustable assembly according to one embodiment.

FIG. 6 shows components of an adjustable assembly according to one embodiment. In FIG. 6, the hinge assembly has an axis 52 along the center of the hinge support 16 to the center of the ring structure 14.

As illustrated in FIG. 6, the left side of the back cover 4 has a circular portion 32 with a circular opening; and the tubular portion 36 of the tubular element 18 is configured to be inserted through the circular opening of the circular portion 32 of the back cover 4 near the hinge support 16 and inserted into the hinge support 16. The circular portion 32 of the back cover 4 is configured to be sandwiched between the hinge support 16 and an end portion of the tubular element 18. Thus, the left side of the back cover 4 can rotate freely about relative to the hinge support 16.

As illustrated in FIG. 6, a circular bracket 40 is configured to be attached to the back cover 4. A left end 38 of a tubular component 46 of the locking mechanism 20 is hingedly coupled with the circular bracket 40 such that the left end 38 of the tubular component 46 can rotate within the circular bracket 40.

As illustrated in FIG. 6, the tubular component 46 of the locking mechanism 20 has a tooth portion 44. A spring element 42 is coupled between the circular bracket 40 and the tooth portion 44 to push the tubular component 46 of the lock mechanism 20 towards the ring structure 14.

As illustrated in FIG. 6, the right end 50 of the tubular component 46 of the locking mechanism 20 has a key 48. The right end 50 with the key 48 is to be inserted into the opening of the ring structure 14 through an opening in a tooth portion 34 at the right side of the back cover 4. Thus, the tooth portion 34 of the back cover 4 is configured to be sandwiched between the tooth portion 44 of the tubular component 46 and the ring structure 14.

As illustrated in FIG. 6, the tooth portion 44 of the tubular component 46 has a set of teeth evenly distributed in a circumferential direction relative to the axis 52 of the hinge assemble. The tooth portion 34 of the back cover 4 has a set of teeth corresponding to the set of teeth of the tooth portion 44 of the tubular component 46.

When the teeth of the tooth portion 44 engage with the teeth of the back cover 4, each of the teeth of the tooth portion 44 is inserted between a gap between two teeth of the back cover 4; and each of the teeth of the back cover 4 is inserted between a gap between two teeth of the tooth portion 44. Thus, when the teeth of the tooth portion 44 engage with the teeth of the back cover 4, the tubular component 46 of the locking mechanism 20 is locked to the back cover 4 to prevent the tubular component 46 from rotation about the back cover 4 along the axis 52 of the hinge assembly.

When the tubular component 46 of the lock mechanism 20 is pushed towards to the hinge support 16, the tooth portion 44 moves along the axis 52 of the hinge assembly relative to the teeth of the back cover 4; thus teeth of the tooth portion 44 of the tubular component 46 disengage with the teeth of the back cover 4; and the tubular component 46 of the locking mechanism 20 is then free to rotate along the axis 52 of the hinge assembly relative to the teeth of the back cover 4.

As illustrated in FIG. 6, the key 48 is fixedly coupled on the right end 50 of the tubular component 46. The key 48 is configured to be inserted in a slot in the ring structure 14. The side walls of the slot can contact the side surfaces of the key 48 to limit the rotation of the tubular component 46 of the locking mechanism 20 with respect to the ring structure 14.

When the right end 50 of the tubular component 46 and the key 48 of the tubular component 46 of the lock mechanism 20 are moved in a direction pointing from the hinge support 16 towards the ring structure 14, the gap between the side walls of the slot and the key 48 is reduced and eventually eliminated at a locked position where the contact between the side walls of the slot and the key 48 prevents the key 48 from moving further in the direction pointing from the hinge support 16 to the ring structure 14.

As illustrated in FIG. 6, when the key 48 is at the locked position inside the slot in the ring structure 14, the teeth of the tooth portion 44 are configured to engage with the teeth of the back cover. Thus, when the key 48 is at the locked position inside the slot in the ring structure 14, the tubular component 46 of the locking mechanism 20 is locked to both the ring structure 14 and the back cover 4, via the key 48 and the teeth of the tooth portion 44 respectively; and thus, the support component 2 and the back cover 4 are locked into a particular angular coupling relative to the axis 52 of the hinge assembly.

As illustrated in FIG. 6, the push knob 12 has a click-to-lock portion 66 that can be inserted into the right end 50 of the tubular component 46 of the locking mechanism 20 and click into the opening 64 to attach the push knob 12 to the tubular component 46. Thus, when the push knob 12 is pushed along the direction pointing from the ring structure 14 towards the hinge support 16, the coupling between the click-to-lock portion 66 of the push knob 12 and the opening 64 of the tubular component 46 allows the tubular component 46 of the locking mechanism 20 to be pushed against the spring element 42 to move to an unlocked position, where the teeth of the tooth portion 44 of the tubular component 46 disengage with the teeth of the back cover 4, and a gap is provided between the side walls of the slot in the ring structure 14 and the key 48.

Figure 7:
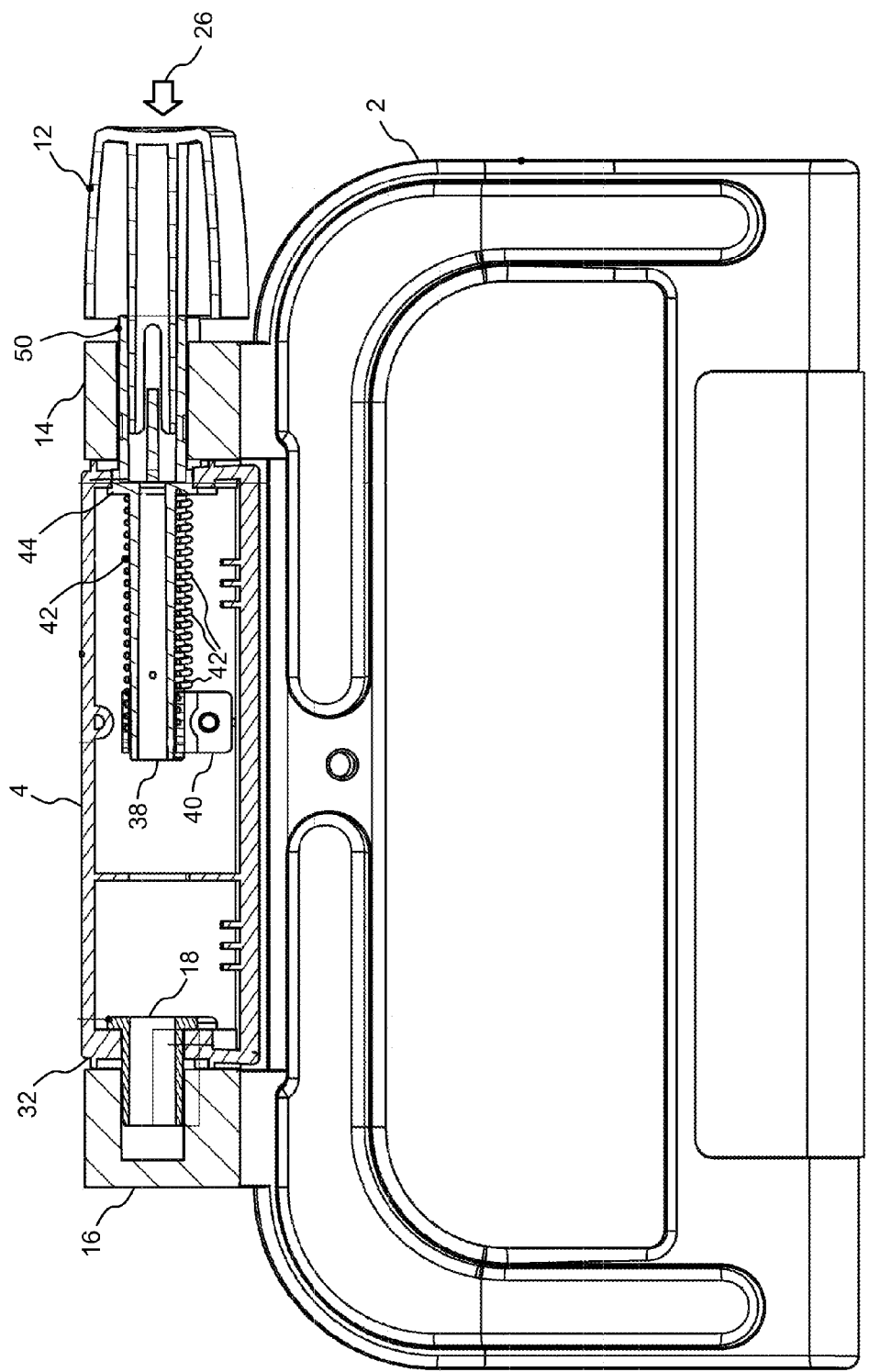
FIGS. 7 and 8 show coupling of components of an adjustable assembly according to one embodiment.
Figure 8:
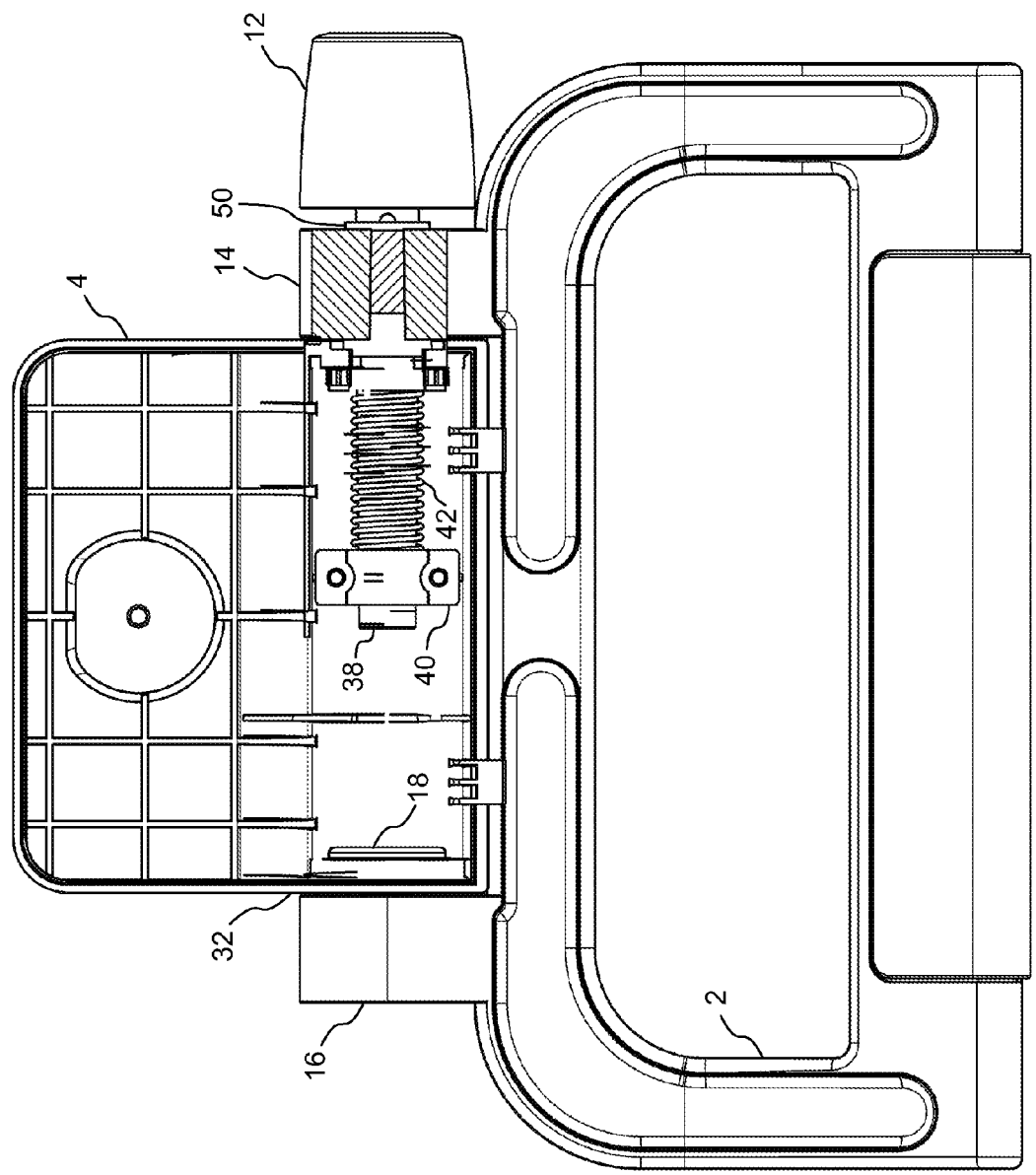

FIGS. 7 and 8 show coupling of components of an adjustable assembly according to one embodiment.

In FIG. 7, a cross section through the axis 52 of the hinge assembly is shown. In FIG. 7, the pushed knob 12 is inserted in and clicked into the right end 46 of the tubular component of the locking mechanism 20. The right end 50 of the tubular component 46 is inserted in the ring structure 14. The spring element 42 pushes the tooth portion 44 of the tubular component 46 of the locking mechanism 20 so that the teeth of the tooth portion 44 engage with the teeth of the back cover 4. The left end 38 of the tubular component 46 of the locking mechanism 20 is in the circular bracket 44 to allow rotation about the axis 52 of the hinge assemble.

In FIG. 7, the push knob 12 can be pushed in a direction 26 to move the tooth portion 44 towards the hinge support 16 and release the angular locking mechanism.

FIG. 8 shows a front view of the back cover 4, with a cross section view of the ring structure.

FIG. 9 shows an exploded view of an adjustable hinge assembly according to one embodiment. The adjustable hinge assembly allows the coupling between two components, such as the tooth portion 34 of the back cover 4 for a display device 10 of a portable ultrasound imaging apparatus 1 and the support component 2 of the portable ultrasound imaging apparatus 1, to be adjusted to, and then locked at, a desirable angle, in accordance with the spacing determined by the number of teeth configured on the tooth portion 44 of the angular locking mechanism 20.

In FIG. 9, the tooth portion 34 of the hinge assembly is illustrated to be connected to the back cover 4 of the housing 6 of a portable ultrasound imaging device. The tooth portion 34 can be connected to other display devices, such as a computer monitor, an all-in-one computer, a touch screen of a portable computer, etc., or other devices.

In FIG. 9, a portion of the support component 2 is not shown. It is understood that the support component 2 can have a shape and design different from the support component 2 illustrated in various figures, such as FIGS. 1, 3-4 and 6.

As illustrated in FIG. 9, the tubular portion 50 is configured to be inserted through the opening of the tooth portion 34 of the component 4 and inserted into the ring structure 14 of the component 2.

The keys 48 on the outer surface of the tubular portion 50 of the tubular component 46 are configured to be inserted into the slots 54 in the ring structure 14 and thus limit and/or eliminate relative rotation between the tubular portion 50 and ring structure 14, with respect to the axis 52 of the hinge assembly.

FIG. 9 illustrates the use of two keys 48 in two slots 54. More or less key/slot pairs can be used in alternative configurations.

As illustrated in FIG. 9, the tubular portion 38 is configured to be inserted into the spring 42 and the circular bracket 40 such that the tubular portion 38 is hingedly coupled with the circular bracket 40.

The circular bracket 40 can be fixedly coupled to one of the component 4 and the component 2 to provide stability for the assembly along the axis 52.

The tooth portion 44 between the tubular portions 38 and 50 is configured to be insertable into the opening of the tooth portion 34 of the component 4. When the tooth portion 44 is inserted into the tooth portion 34, each tooth in the tooth portion 44 is between a corresponding gap between two teeth in the tooth portion 34; and each tooth in the tooth portion 34 is between a corresponding gap between two teeth in the tooth portion 44. The teeth in the tooth portions 44 and 34 are evenly distributed circumferentially about the axis 52. Thus, the tooth portion 44 can be rotated about the axis 52 and then be inserted in the opening of the tooth portion 34 of the component 4. The number of teeth in the tooth portion determines the minimum angle that the tubular component can be rotated between insertions into the opening of the tooth portion 34 of the component 4.

When the tooth portion 44 is not inserted into the opening of the tooth portion 34, the component 4 and the tubular component can be rotate relative to each other along the axis 52.

In FIG. 9, the push knob 12 has two click-to-lock tips 66 for locking to the openings 64 on the tubular portion 50. More or less click-to-lock tips may be used in alternative configurations. In an alternative configuration, the push knob 12 is not used; and the end of the tubular portion 50 may be pushed directly to move the tubular component 46.

After the push knob 12 is locked with the tubular portion 50, the tubular component 46 can be pushed along the axis to compress the spring element 42 to an unlocked position where the tooth portion 44 of the tubular component is not in the opening of the tooth portion 34 of the component 4.

When the push knob 12 is not pressed, the spring element 42 is configured to press the tooth portion 44 such that, when the teeth of the tooth portion 44 of the tubular component 46 is aligned with the tooth portion 34 of the component 4, the tooth portion 44 is inserted into the opening of the tooth portion 34 of component 4.

In FIG. 9, the key 48 has a circumferential width that is smaller at an end close to the push knob 12 and larger at an opposite end. Thus, when the key 48 is inserted into the slot 54 along the axis, a gap between the side surfaces of the key 48 and the side walls of the slot 54 is reduced and eventually eliminated when the key 48 is a locked position in the slot 54, as further illustrated in FIG. 14.

FIGS. 10 to 14 illustrate a mechanism to adjust a hingedly coupling angle according to one embodiment.

Figure 10:
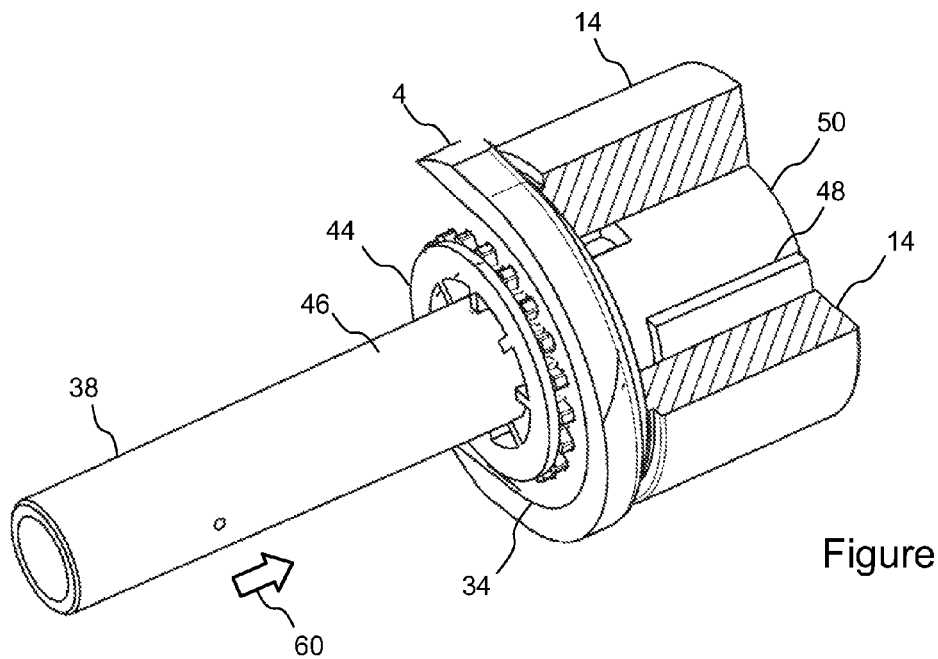
FIGS. 10 to 14 illustrate a mechanism to adjust a hingedly coupling angle according to one embodiment.

FIG. 10 illustrates a locked position where the tooth portion 44 of the tubular component 46 is inserted in the direction 60 into the opening of the tooth portion 34 of the component 4. The contacting between the teeth of the tubular component 46 and the teeth of the component 4 prevents the component 4 from rotating with respect to the tubular component 46; and the contacting between the side surfaces of the key 48 and side walls of the slot 54 in the ring structure 14 prevents the component 2 from rotating with respect to the tubular component.

Figure 11:
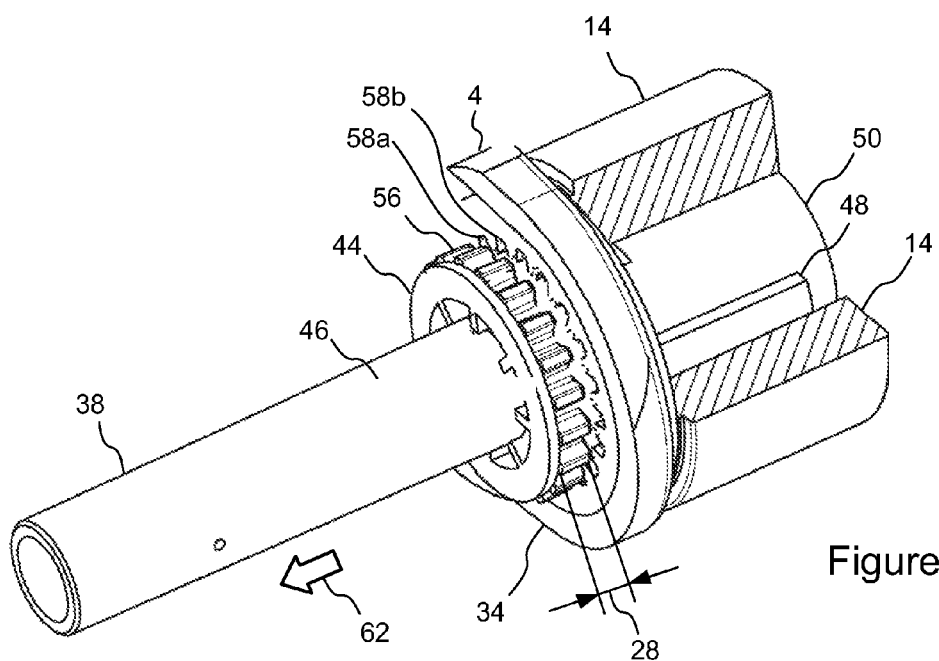

FIG. 11 illustrates a unlocked position, after the tubular component moves a distance 28 along the direction 62 relative to the tooth portion 34 of the component 4. Since the teeth of the tubular component 46 and the teeth of the component 4 are not in contact with each other, the component 4 is free to rotate with respect to the tubular component 46 and thus the component 2; and a gap is provided between the side surfaces of the key 48 and side walls of the slot 54 in the ring structure 14.

Figure 12:
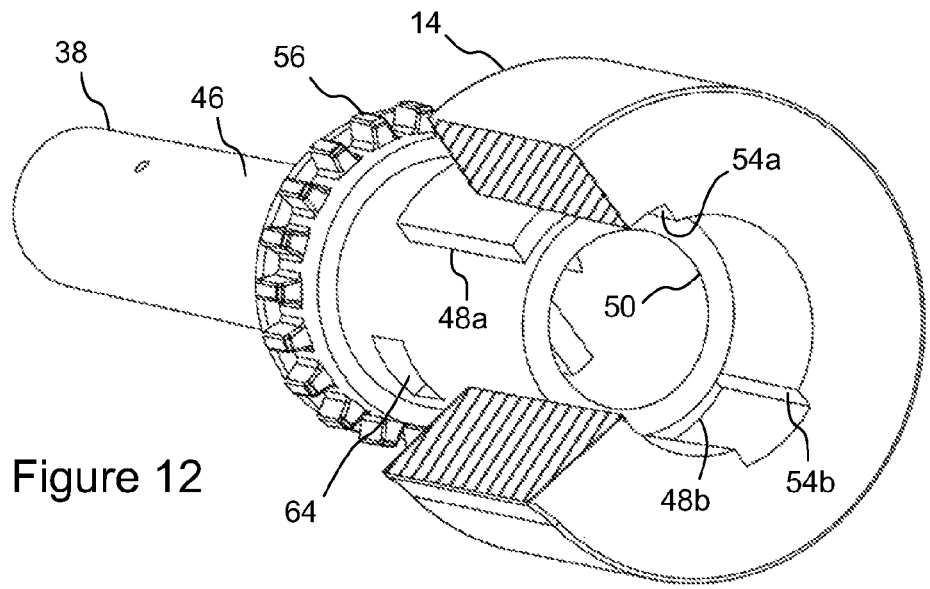

In FIG. 12, a portion of the ring structure 14 and the tooth portion 34 of the component 4 are not shown to illustrate the keys 48a and 48b in the respective slots 54a and 54b in the ring structure 14 in a unlocked position.

Figure 13:
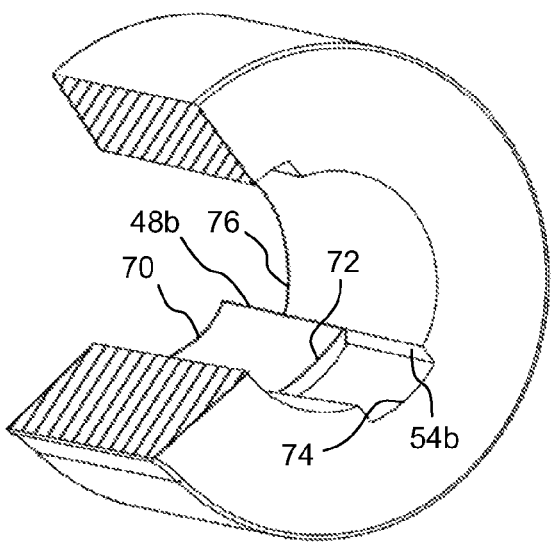

FIG. 13 illustrates the key 48b in the slot 54b. In FIG. 13, the circumferential width 72 of the end of the key 48b in the slot is smaller than the circumferential width 70 of the opposite end of the key 48b; and the circumferential width of the slot 54a at the end 74 is small than the circumferential width of the slot 54a at the end 76. Thus, the more key 48b is inserted into the slot 54b towards the end 74, the smaller is the circumferential gap between the key and the side walls of the slot 54b.

Figure 14:
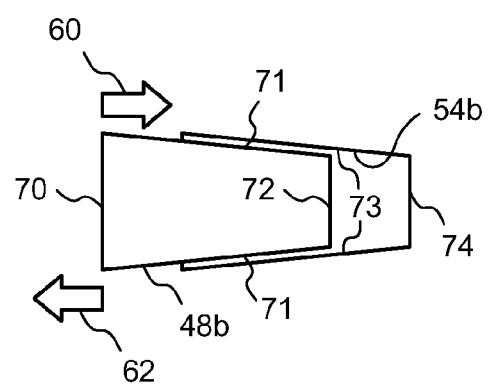

FIG. 14 shows a top view of the key 48a in relation with the slot 54b. In FIG. 14, there is a gap between the side surfaces 71 of the key 48b and the side walls 73 of the slot 54b. Since the width 70 of the left end of the key 14 is larger than the width 72 of the right end of the key 14, the gap is reduced when the key 48b is moved into the slot 54b in the direction 60. When the key 48b moves in the direction 60 to a position where the slot 54b having a shape matching the shape of the key 48b, the gap is eliminated and the key 48b cannot move further in the direction 60. When the key 48b moves to in the direction 62, the gap is provided and increased.

Eliminating the gap between the side surfaces of the key 48 and the side walls of the slot 54 eliminates unwanted rotation between the components 2 and 4 when the hinge assembly is in the locked position.

Optionally, the thickness (or height in the radial direction about the axis 25) of the key 48b can also be configured to vary from small at the end 72 to large at the end 70. The depth of the slot 54b varies from small to large according to the thickness profile of the key 48b, such that when the key 48b is inserted into the slot, the top surface of the key 48b is in contact with the roof of the slot 54b, in a way similar to the side surfaces of the key 49b in contact with the side walls of the slot 54b.

Figure 15:
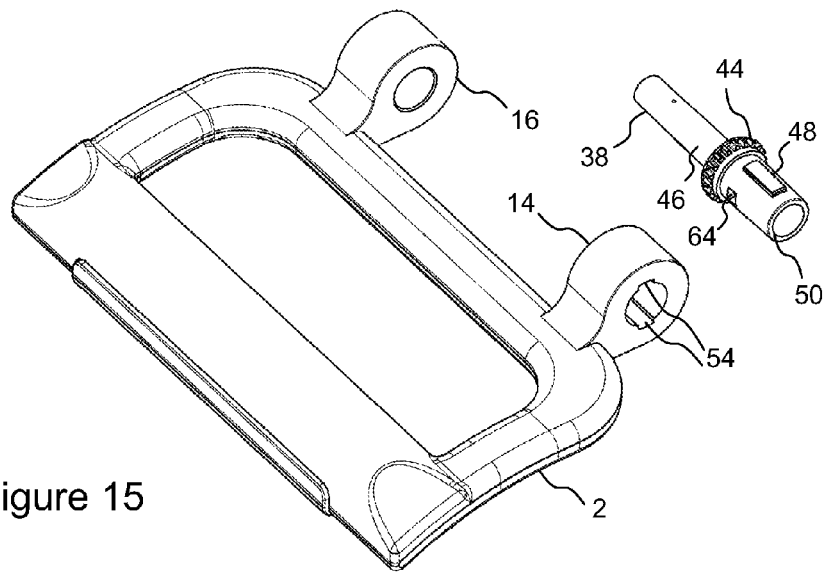
FIGS. 15 to 17 show structural details of components of an adjustable hinge assembly according to one embodiment.
Figure 16:
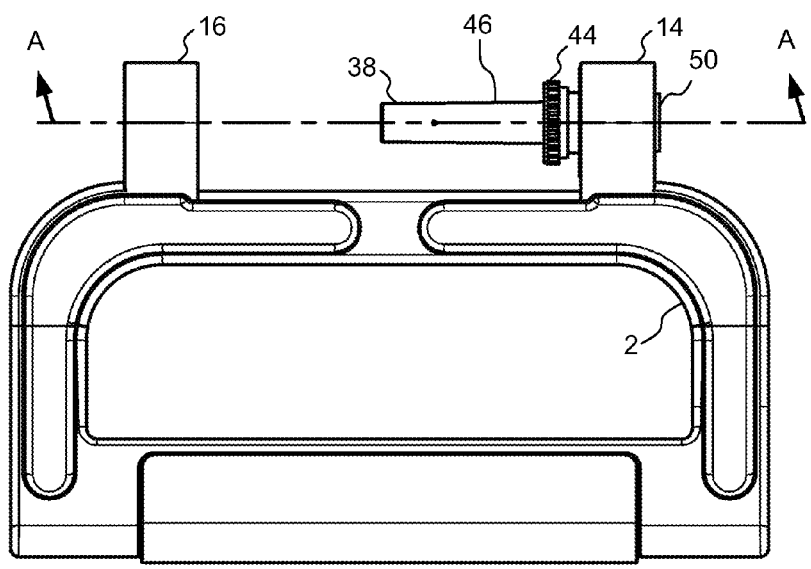
Figure 17:
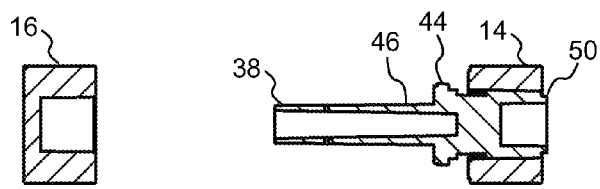

FIGS. 15 to 17 show structural details of components of an adjustable hinge assembly according to one embodiment.

FIG. 15 shows a view of the support component 2 in relation with the tubular component 46 of the locking mechanism 20. The support component 2 has the hinge support 16 and the ring structure 14. The tubular component 46 of the locking mechanism 20 has tubular portions 38 and 50, the keys 48, the tooth portion 44, and openings 64 for coupling with click-to-lock tips 66 of the push knob 12. The ring structure 14 has slots 54 for the respective keys 48.

FIG. 16 shows a view of the tubular component 46 being inserted into the ring structure 14 of the support component 2. A cross section view, along the line A-A, of the hinge support 16 the tubular component 46 and the ring structure 14 is provided in FIG. 17.

In the foregoing specification, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

What is claimed is:

1. A portable ultrasound imaging apparatus, comprising:
   a housing;
   a display device amounted on the housing;
   a processor disposed within the housing and coupled with the display device to present ultrasound images;
   a beamformer disposed within the housing and coupled with the processor to control an ultrasound transducer;
   a support component hingedly coupled with the housing to allow the support component to rotate with respect to the housing about an axis parallel to an edge of the display device; and
   an adjustable assembly coupled between the support component and the housing;
   wherein when the adjustable assembly is in a first configuration, the support component is locked to the housing with respect to rotation about the axis;
   wherein when the adjustable assembly is in a second configuration, the support component is rotatable about the axis with respect to the housing;
   wherein the adjustable assembly includes
      a key extending in parallel to the axis; and
      walls extending in parallel to the key to define a slot configured to accommodate the key;
   wherein when the key moves in a first direction parallel to the axis to a first position in the slot, at least a portion of side surfaces of the key is in contact with the walls to prevent the key from moving in the slot in the first direction beyond the first position;
   wherein when the key is at the first position in the slot, the adjustable assembly is locked in the first configuration, and the key is movable in a second direction opposite to the first direction to a second position in the slot to provide a gap between the walls and the side surfaces of the key; and
   wherein when the key is at the second position in the slot, the adjustable assembly is in the second configuration and allows the support component to rotatable about the axis with respect to the housing.

2. The portable ultrasound imaging apparatus of claim 1, wherein the key has a first end and a second end; the key extending from the first end to the second end in the first direction; a width of the second end of the key is smaller than a width of the first end of the key; the side surfaces of the key extends from the first end to the second end; and the side surfaces are separated in a circumferential direction about the axis.

3. The portable ultrasound imaging apparatus of claim 2, wherein a height of the second end of the key in a radial direction about the axis is smaller than a height of the first end of the key in the radial direction about the axis.

4. The portable ultrasound imaging apparatus of claim 2, wherein when the key is at the first position in the slot, a distance between the walls at the first end of the key is equal to the width of the first end of the key, and a distance between the walls at the second end of the key is equal to the width of the second end of the key.

5. The portable ultrasound imaging apparatus of claim 4, wherein the adjustable assembly includes a spring element configured to push the key in the first direction.

6. The portable ultrasound imaging apparatus of claim 5, wherein the adjustable assembly further includes a push knob configured to be pushed by a user against the spring element to move the key in the second direction.

7. The portable ultrasound imaging apparatus of claim 6, wherein when the key is at the first position in the slot, the gap is eliminated.

8. The portable ultrasound imaging apparatus of claim 6, wherein the an adjustable assembly further includes a first set of teeth and a second set of teeth corresponding to the first set of teeth;
   wherein both the first set of teeth and the second set of teeth are evenly distributed in a circumferential direction about the axis;
   wherein when the key is at the first position in the slot, the first set of teeth engages with the second set of teeth to lock the support component to the housing with respect to rotation about the axis; and
   wherein when the key is at the second position in the slot, the first set of teeth disengages with the second set of teeth to allow the support component rotate about the axis with respect to the housing.

9. The portable ultrasound imaging apparatus of claim 8, wherein the housing includes a back cover; the walls defining the slot are fixedly coupled with the support component; the first set of teeth is fixedly coupled with the back cover; and the second set of teeth is fixedly coupled with the key.

10. The portable ultrasound imaging apparatus of claim 9, wherein adjustable assembly further includes a tubular component having a first end and a second end; the first end of the tubular component is hingedly coupled with the back cover and rotatable about the back cover along the axis; and the key is on an outer surface of the second end of the tubular component.

11. The portable ultrasound imaging apparatus of claim 9, wherein the second set of teeth is formed on the tubular component.

12. A portable display apparatus, comprising:
a display device;
a support component hingedly coupled with the display device to allow the support component to rotate with respect to the display device along an axis; and
an adjustable assembly coupled between the support component and the display device, the adjustable assembly including
  a key having a first end and a second end, the key extending from the first end to the second end in a first direction parallel to the axis, the key having side surfaces extending from the first end to the second end, the side surfaces of the key separated by a distance in a circumferential direction about the axis; and
  walls substantially in parallel with the side surfaces of the key to define a slot for the key;
wherein when the key moves along the first direction to a first position in the slot, contacting between at least a portion of the side surfaces of the key and the walls prevents the key from moving in the first direction in the slot beyond the first position;
wherein when the key is at the first position in the slot, the key is movable only in a second direction opposite to the first direction, the key movable in the second direction to a second position in the slot;
wherein when the key is at the first position in the slot, the support component is locked to the display device with respect to rotation along the axis; and
wherein when the key is at the second position in the slot, the support component is rotatable along the axis with respect to the display device.

13. The portable display apparatus of claim 12, wherein a width of the second end of the key is smaller than a width of the first end of the key.

14. The portable display apparatus of claim 13, wherein when the key is at the first position in the slot, a distance between the walls at the first end of the key is equal to the width of the first end of the key, and a distance between the walls at the second end of the key is equal to the width of the second end of the key.

15. The portable display apparatus of claim 14, wherein the adjustable assembly includes:
a spring element configured to push the key in the first direction;
a push knob configured to be pushed by a user against the spring element to move the key in the second direction;
a first set of teeth evenly distributed along a circumferential direction about the axis; and
a second set of teeth evenly distributed along a circumferential direction about the axis;
wherein when the key is at the first position in the slot, the first set of teeth are in gaps between second set of teeth, and the second set of teeth are in gaps between first set of teeth to look the support component to the display device with respect to rotation about the axis; and
wherein when the key is at the second position in the slot, the first set of teeth and the second set of teeth are not in contact with each other to allow the support component to rotate about the axis with respect to the display device.

16. The portable display apparatus of claim 15, wherein the display device includes a back cover; the first set of teeth is fixedly coupled with the back cover; the walls defining the slot are fixedly coupled with the support component; and the second set of teeth is fixedly coupled with the key.

17. The portable display apparatus of claim 16, wherein adjustable assembly further includes a tubular element having a first end and a second end; the first end of the tubular component is hingedly coupled with the back cover and rotatable about the back cover along the axis; and the key is positioned on an outer surface of the second end of the tubular component.

18. The portable display apparatus of claim 16, wherein the set of teeth is formed on the tubular component; and the component defining a set of slots is disposed along the axis between the set of teeth and the key.

19. An adjustable hinge assembly, comprising:
a tubular component having a first end and a second end, the tubular component extending from the first end to the second end in a first direction along an axis and having
  a key formed on the second end and extending in parallel to the axis, the key having side surfaces extending in the first direction and separated by a distance in a circumferential direction about the axis; and
  a plurality of first teeth evenly distributed in the circumferential direction about the axis;
a first component having a ring structure defining an opening configured to accept the second end of the tubular component, the ring structure having walls extending in the first direction and separated by a distance in the circumferential direction about the axis, the walls defining a slot for the key;
a second component having a plurality of second teeth corresponding to the plurality of the first teeth and evenly distributed in the circumferential direction about the axis;
a spring element configured to push the tubular component in the first direction; and
a push knob coupled with the second end of the tubular component to allow a user to push against the spring element to move the tubular component in a second direction opposite to the first direction;
wherein when the spring element pushes the tubular component in the first direction to a first position,
  contacting between the side surfaces of the key and the walls prevents the tubular component from moving further in the first direction beyond the first position, and
  the plurality of first teeth engages with the plurality of second teeth to lock the first component with respect to the second component with respect to rotation about the axis;
wherein when the push knob is pushed to move tubular component in the second direction to a second position,
  a gap is provided between the side surfaces of the key and the walls defining the slot, and the plurality of first teeth disengages with the plurality of second teeth to allow the first component to rotate about the axis relative to the second component.

20. The adjustable hinge assembly of claim 19, wherein the key has a first key end and a second key end; the key extending from the first key end to the second key end in the first direction; the side surfaces are separated by
a first distance in the circumferential direction about the axis at the first key end, and
a second distance in the circumferential direction about the axis at the second key end;
wherein the first distance is larger than the second distance.

\* \* \* \* \*